United States Patent
Song et al.

(10) Patent No.: US 11,835,770 B2
(45) Date of Patent: Dec. 5, 2023

(54) AUTOMATED FIBER OPTIC ROTARY JOINT

(71) Applicant: ChiSquare Bioimaging LLC, Brookline, MA (US)

(72) Inventors: Loling Song, Chestnut Hill, MA (US); Hendrik van Gorsel, Chestnut Hill, MA (US)

(73) Assignee: ChiSquare Bioimaging LLC, Framingham, MA (US)

( * ) Notice: Subject to any disclaimer, the term of this patent is extended or adjusted under 35 U.S.C. 154(b) by 497 days.

(21) Appl. No.: 17/156,600

(22) Filed: Jan. 24, 2021

(65) Prior Publication Data

US 2021/0239911 A1 Aug. 5, 2021

Related U.S. Application Data

(60) Provisional application No. 62/965,562, filed on Jan. 24, 2020.

(51) Int. Cl.
| | |
|---|---|
| *G02B 6/36* | (2006.01) |
| *A61B 5/00* | (2006.01) |
| *A01K 29/00* | (2006.01) |
| *A61N 5/06* | (2006.01) |

(52) U.S. Cl.
CPC .......... *G02B 6/3604* (2013.01); *A01K 29/005* (2013.01); *A61B 5/6868* (2013.01); *A61N 5/0622* (2013.01)

(58) Field of Classification Search
None
See application file for complete search history.

(56) References Cited

U.S. PATENT DOCUMENTS

| | | | |
|---|---|---|---|
| 4,943,137 A | 7/1990 | Speer | |
| 5,039,193 A | 8/1991 | Snow | |
| 6,301,405 B1 | 10/2001 | Keil | |
| 8,903,476 B2 | 12/2014 | Brennan | |
| 8,985,057 B2 * | 3/2015 | Woodward | A61B 5/4848 119/421 |
| 9,360,630 B2 | 6/2016 | Jenner | |
| 10,884,199 B2 | 1/2021 | Altshuler | |
| 11,412,932 B1 * | 8/2022 | Peng | A61B 5/0042 |

* cited by examiner

*Primary Examiner* — Omar R Rojas
(74) *Attorney, Agent, or Firm* — Patent GC LLC (57) ABSTRACT

An automated fiber optic rotary joint (FORJ) dynamically measures, using an angle encoder, twists in an optical fiber cable caused by movements of a mouse or other animal and automatically unwinds the optical fiber cable(s) by engaging a motor. To optimize its efficiency, the unwinding process is activated automatically only when the angle encoder reaches a predetermined threshold. In some embodiments, the optical fiber is unwound in increments of 360°. Various embodiments allow simultaneous transfer of optical signals through independent channels to and from multiple sites of a freely moving animal through a rotating interface and with minimal mechanical impact on the natural behavior of the animal. The design principle leads to a minimal variation of light transmission over rotation suitable for life science applications. A single channel FORJ device can be readily expanded to a two-, three- or more-channel device.

20 Claims, 7 Drawing Sheets

AUTOMATED FIBER OPTIC ROTARY JOINT

STATEMENT REGARDING FEDERALLY SPONSORED RESEARCH OR DEVELOPMENT

This invention was made with government support under grant number 1R43AA028146-01 awarded by the National Institutes of Health. The government has certain rights in the invention.

CROSS-REFERENCE TO RELATED APPLICATIONS

This application is a non-provisional patent application of U.S. Provisional Patent Application Ser. No. 62/965,562, filed Jan. 24, 2020, entitled "Automated Fiber Optic Rotary Joint", which is hereby incorporated by reference.

BACKGROUND

Technical Field

The present invention relates to fiber optic rotary joints and, more particularly, to a single or multiple-channel fiber optic rotary joint (FORJ) capable of actively releasing torsion in optical cables.

Related Art

Since the first fiber optics-based recording systems (fiber photometry) were demonstrated, the fiber photometry technique has gained wide-spread adoption in the neuroscience community. An optical fiber is inserted to any depth in the brain of a mouse or other small animal, and it delivers light to and/or collects light from a group of cells at the fiber tip. The small fiber size and minimal weight make fiber photometry minimally invasive.

Currently there is no multi-channel bidirectional fiber optic rotary joint (FORJ) that is suitable for small animals (such as mice) in neuroscience or other life science applications. Such FORJs must have low transmission variation over rotation, i.e., the difference between the highest and lowest light transmission efficiency over a full 360° rotation. Such FORJs must also exhibit sufficiently low starting torque for small animals such as mice. Most of the commercially available single and multi-channel FORJs are designed for telecommunication use and are not suitable for neuroscience or life science applications. Specifically, these commercial FORJs exhibit large transmission variation over rotation, which obscures the weak fluctuation of the biological signals, and the high starting torque impacts the natural behavior of a small animal such as a mouse. In order for a FORJ to be suitable for life science applications, it must have very small variation in the transmitted light over a 360° rotation relative to the magnitude of biologically relevant optical signals, and the starting torque must be significantly reduced by at least two orders of the magnitude compared to that of a FORJ for telecommunication.

SUMMARY

An embodiment of the present invention provides an automated fiber optic rotary joint. The automated fiber optic rotary joint includes a processor.

An electric motor is communicably coupled to the processor for control by the processor.

A shaft is mechanically coupled to the electric motor for rotation by the motor.

A sensor is configured to detect rotational position of the shaft. The sensor is communicably coupled to the processor to provide information to the processor about the angular position of the shaft.

A first arm or disk is rigidly coaxially attached to the shaft for rotation with the shaft.

A second arm or disk is axially spaced apart from the first arm or disk. The second arm or disk is coaxially disposed about the shaft, such that the shaft can rotate independently of the second disk.

A clutch is coupled to the processor for control by the processor. The clutch is configured to selectively mechanically couple the second arm or disk to the shaft for rotation with the shaft.

A first optical element has a first port, a second port and a common port. The first port may, for example, be an input port, where excitation light from an excitation light source enters the first optical element, which may, for example, be a beam splitter. The excitation light exits the beam splitter via the common port, and light 1 emitted from a test animal enters the beam splitter via the common port and exits the beam splitter via the second port.

An interlocking alignment mechanism is configured to ensure that the second arm or disk maintains its originally well-defined(x, y) position and its surface substantially parallel to the surface of the first optical element whenever the clutch is disengaged.

A first optical fiber extends between the first arm or disk and the second arm or disk. Where a first end of the first optical fiber is optically aligned with the first port of the first optical element is considered to be the calibrated rotational and horizontal position of the second arm or disk.

The processor is configured to automatically use the information about the angular position of the shaft to determine whether the first arm or disk has rotated by a first predetermined amount. If the processor detects that the shaft has rotated the first predetermined amount, the processor is configured to automatically cause: (a) the clutch to engage, (b) the motor to rotate the shaft by a second predetermined amount in a direction same as rotation of the first arm or disk and then (c) the clutch to disengage.

In any embodiment, the motor may include a motor having substantially no resistance to rotation.

In any embodiment, the first optical fiber may be replaceably attached to the first arm or disk and to the second arm or disk.

Any embodiment may also include a second optical fiber, a first end of which is optically coupled to a second end of the first optical fiber. The second optical fiber extends from the first arm or disk.

In any embodiment with a second optical fiber, the second optical fiber may be replaceably attached to the first arm or disk.

In any embodiment with a second optical fiber, a second end of the second optical fiber may be configured to be a part of or connected to an implant in a living rodent brain or any anatomical region of choice in a small animal.

In any embodiment, the second predetermined amount may be an integer multiple of 360°.

In any embodiment, the second predetermined amount may be about a fraction n/m of 360°, with n being an integer and m a number of analysis channels.

In any embodiment, the brake may include a frame member configured to support the second arm or disk. The clutch may have a clamp that is attached to the second arm and can be configured to grab onto the motor shaft, thereby rotating the second arm. In any embodiment, the clutch may also include an electromagnet configured to raise the second arm or disk from the frame member. Alternatively, in any embodiment, the clutch may include a master gear attached to the motor shaft. A servo horn is controlled by a servo motor which is attached to the second arm. In the default state in which the second arm is stationary, the master gear is not engaged with the servo horn. Upon instruction from the processor, the servo motor moves the servo horn by an angle in the plane parallel to the plane of the second arm such that the master gear and the servo horn are engaged.

In any embodiment, the second arm may have a bottom and the frame member may have a top. Sawtooth structures may be formed on the bottom of the second arm and on the top of the frame member. Alternatively or in addition, structure may be formed on the bottom of the second arm and on the top of the frame member that allow for reproducible and accurate positioning and repositioning. In any embodiment, the second arm may have a side surface facing a side surface of the frame member. Any interlocking alignment methods may be formed between the side surface of the second arm and a side surface of the frame member that allow for reproducible and accurate positioning and repositioning.

Any embodiment may also include a second optical beamsplitter or optical element having a first port, a second port and a common port. A third optical fiber may extend between the first arm or disk and the second arm or disk. At the predetermined rotational position of the second arm or disk, a first end of the third optical fiber is optically aligned with the first port of the second optical beamsplitter or optical element.

Any embodiment may also include a third optical beamsplitter or optical element having a first port, a second port and a common port. A fourth optical fiber may extend between the first arm or disk and the second arm or disk. At the predetermined rotational position of the second arm or disk, a first end of the fourth optical fiber is optically aligned with the first port of the third optical beamsplitter or optical element.

In any embodiment, the second arm or disk may be configured such that, at the predetermined rotational position of the second arm or disk, the first end of the first optical fiber is optically coupled via free space with the first port of the first optical beamsplitter or optical element.

In any embodiment, the first arm may include a first disk and the second arm may include a second disk.

In any embodiment, the first optical element may include a beamsplitter.

BRIEF DESCRIPTION OF THE DRAWINGS

The invention will be more fully understood by referring to the following Detailed Description of Specific Embodiments in conjunction with the Drawings, of which.

DETAILED DESCRIPTION

The inventive embodiments disclosed herein address an urgent need for approaches that allow minimally invasive long term optical recording. Simultaneous recordings at multiple sites would allow scientists to gain new insights by constructing a global view on the timing and synchrony of biochemical signals among different brain regions or any anatomical regions of interest. It is to be noted that the term "mouse" or "rodent" when used herein is only used as an example and could refer to any small animal. Further, the claimed invention is not limited to recordings at sites in a brain. The term "brain" is used as an example. The invention can be used for recordings at any anatomical region of interest.

Disclosed herein is an automated fiber optic rotary joint (FORJ) that allows the simultaneous transfer of optical signals to and from multiple sites through a rotating interface and with minimal mechanical impact on the natural behavior in a freely moving animal, such as a rodent. The invention may be used in single and multichannel FORJs. The invention may also be used in uni- and bi-directional FORJs. In a nutshell, the design principle is to dynamically measure, using an angle encoder, twists in an optical cable caused by the movement of a freely moving animal, such as a mouse, and automatically release the torsion in the optical cable by engaging a motor to unwind the twisted optical fiber. In one embodiment, the optical fiber is unwound by an integer multiple of 360° turns. In other embodiments, the optical fiber may be unwound by any desired angular rotation. In yet another embodiment, to optimize its efficiency, the unwinding process is activated automatically only when the angle encoder reaches a predetermined threshold.

The invention is quantitatively characterized as to the overall light throughput, transmission variation over rotation, starting torque, and synchronization of the FORJ with data acquisition. This invention takes a unique approach by combining optical design and rotational sensing to reduce the optical design complexity and reduce the number of mechanical moving parts in order to improve signal-to-noise ratio.

One embodiment of the invention is a multichannel fiber optic rotary joint (FORJ). The invention may be used with FORJs that have uni- or bi-directional optics. The functional characteristics of prior art devices that the inventors have researched do not meet all the requirements needed for life science applications, namely having the capability of transferring optical signals through multiple parallel independent channels with a minimal starting torque suitable for a small animal such as a mouse, and with minimal variation in transmission over the 360° rotation, relative to the weak biologically relevant optical signals compared to the optical noise arising from various sources within the mechanism of a FORJ.

The inventive embodiments disclosed herein provide a FORJ that addresses all the requirements described above. The aim of the disclosed embodiments is to minimize the starting torque and release torsion generated by twisting fibers while maintaining minimal artifacts in optical signals. The rotation of the optical fiber due to movements of the mouse is sensed by a rotary encoder, but the light path does not change till the unwinding process starts, thus there is no FORJ induced variation in light transmission over rotation. The unwinding process is automated to greatly reduce the duration and frequency of experimental interruption. Such a FORJ makes possible long-term behavioral experiments involving freely moving small animals. The strength of the proposed multichannel bidirectional FORT is that our design reduces the optical design complexity to one rotating interface and eliminates the requirement for micrometer scale precision optical alignment. Furthermore, by rotating in increments of 360° we eliminate the transmission variation over rotation that reduces the signal-to-noise ratio in the generally weak biological signals.

The design disclosed herein is novel and, to the inventors' knowledge, is the first of its kind, to make a FORJ an active device instead of a passive device as is found in the prior art.

The optical design disclosed herein improves signal-to-noise ratio through reduction of transmission variation over rotation. Furthermore, by reducing the number of optical interfaces and the number of mechanical moving parts to a single rotating interface with free-space optics that does not require micrometer-scale optical alignment, variation in transmission over rotation is significantly reduced.

The optical design complexity of commercial FORJs scales with the number of channels. This limitation is not inherent in the design disclosed herein. Combining optical design with rotational sensing creates a multi-channel bidirectional FORJ that automatically unwinds the twist of a group of multiple fibers at a predetermined increment, such as increments of 360°.

By utilizing motors with near zero resistance to rotation, the startup torque is significantly reduced.

Two-Channel FORJ

Figure 1A:
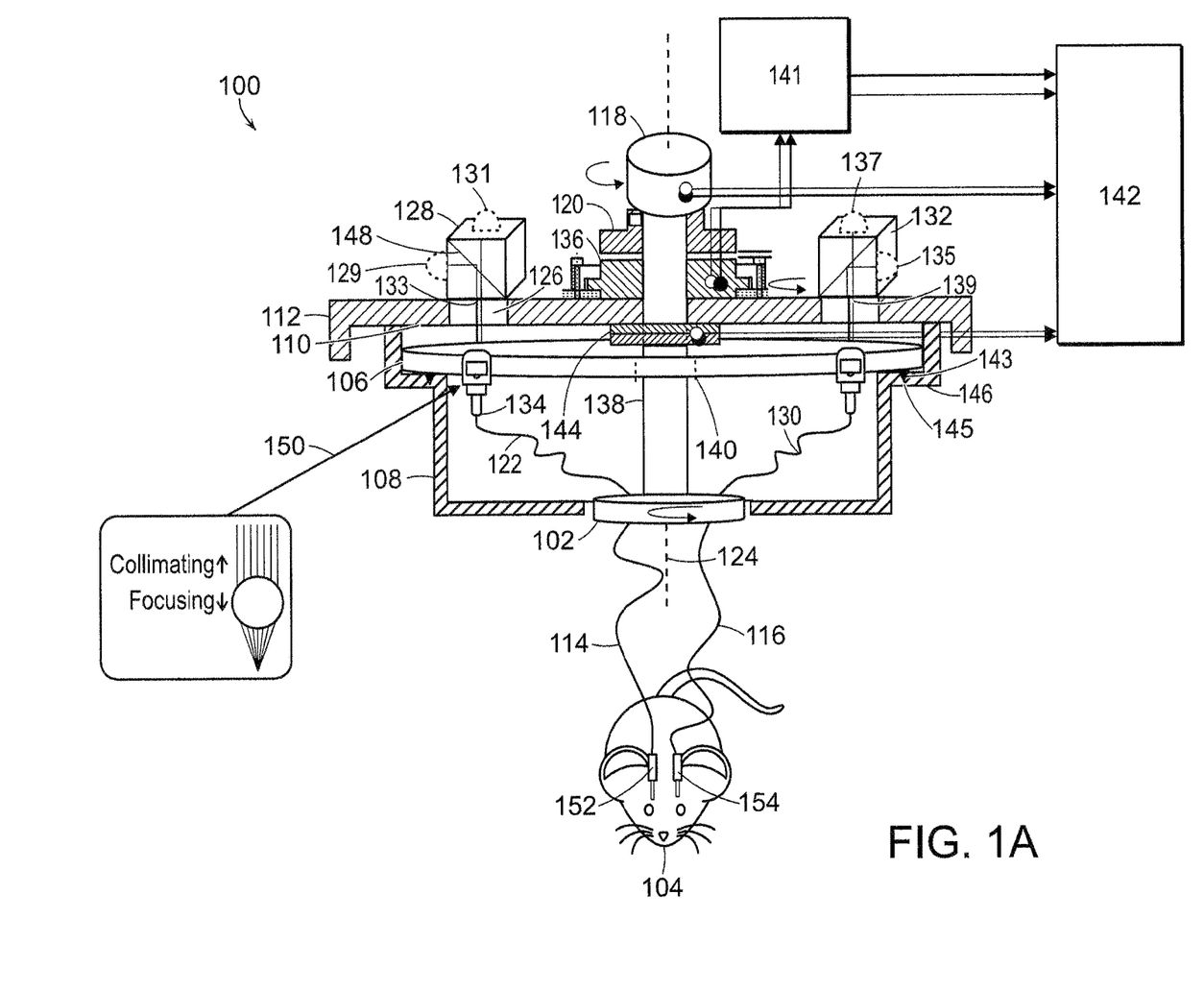
FIG. 1A depicts a side view of an illustrative embodiment of the present invention.

The inventors have designed a two- or more channel FORJ that solves fiber twisting and minimizes variation in light transmission over rotation generated by a freely moving small animal, such as a mouse. FIG. 1A is a side view of an embodiment of an inventive fiber optic rotary device 100 not drawn to scale and illustrates the design principle. The FORJ 100 includes two concentric arms or disks—one freely rotatable arm (also referred to as the first arm) 102 that rotates as an animal 104 moves and one motorized arm (also referred to as the second arm) 106. The freely rotatable arm 102 is attached to the shaft 138 which in turn rotates the rotor 120. In one embodiment, the rotatable arm 102 is rigidly attached to the shaft 138 such that the rotatable arm 102 and shaft 138 rotate together. A dark enclosure 108 can be built around the motorized disk or second arm 106 on the bottom side 110 of the lid 112 to cut ambient light. In the embodiment shown in FIG. 1A, the lid 112 is the lid to the cage of the animal 104. In other embodiments, the lid 112 may be any planar surface that is used to support the other elements of the FORJ 100 and the FORJ 100 can be used with an existing top of a cage or other enclosure.

The motorized arm 106 is axially spaced from the first arm 102 and coaxially disposed about the shaft 138, such that the shaft 138 can rotate independently of the motorized arm 106.

This design dynamically measures, using a sensor such as an angle encoder, the winding of one or more optical fiber cables 114, 116 that extend to a freely-moving animal 104 and automatically releases the torsion in the optical cables 114, 116 by engaging a motor 118 to rotate the rotor 120 by a predetermined amount. The rotor 120 and stator 136 work in combination with an encoder electronics module 141 to function as a rotary encoder or angle encoder (sensor). Any known angle encoder or sensor that can measure angular displacement may be used to measure the rotation of the first arm 102 and shaft 138. The sensor is configured to detect the angular position of the shaft 138 and is communicably coupled to the processor 142 to provide information about the angular position of the shaft 138 to the processor 142. The motor 118 is communicably coupled to and controlled by the processor 142. The shaft 138 is mechanically coupled to the motor 118 such that the shaft 138 is rotated by the motor 118. In one embodiment, the motor 118 rotates the rotor 120 by an integer multiple of 360° turns.

The first optical fiber 122 (between the two arms or disks 102 and 106) is designed to be long and loose enough to allow the rotatable disk or first arm 102 to freely rotate in either direction. The first optical fiber 122 may be fixed to one or both of the arms 102, 106 or may be replaceably attached to one or both of the arms 102, 106. In the embodiment shown in FIG. 1A, the first optical fiber 122 is coupled to the motorized arm 106 via the optical element 150. A second optical fiber 114 and is optically coupled to the first optical fiber 122 and extends from the first optical fiber 122 in the rotatable disk or first arm 102 to the animal 104. The second optical fiber 114 may also be fixed or replaceably attached. As the animal 104 moves about, in particular as the animal 104 moves about in circles, the second optical fiber 114 becomes twisted. The twists on the second optical fiber 114 exerts torque on the rotatable disk or arm 102 and leads to the rotation of the rotatable disk or first arm 102. The encoder functions as a sensor and measures rotation of the rotatable arm or first disk 102. The device 100 unwinds only when the measured angle reaches a predetermined value, i.e., when the rotation angle reaches or exceeds a predetermined value. While a first optical fiber 122 (between the two arms) and a second optical fiber 114 (between the first arm and the mouse) are disclosed herein, it is expressly contemplated that the first and second optical fiber 122, 114 may be combined into a single optical fiber.

The first key aspect of the design disclosed herein is to reduce the complexity of the design, thereby limiting the number of sources of optical noise due to optical and mechanical alignments, and minimizing the number of interfaces to a single free-space optical interface per channel between the stationary portion and rotating portion of the FORJ 100. A free-space interface 126 sits within a collimated optical path and eliminates transmission variation over rotation—a key limitation of the current commercial FORJs. In the sections below, it is disclosed how both the duration and frequency of experiment interruption due to automated unwinding are minimized.

Through the free-space optical interface 126, the first optical fiber 122 is optically aligned with a first port 129 and a second port 131 of a first optical element 128. A third optical fiber 130, as described below, may be optically aligned with a first port 135 and a second port 137 of a second optical element 132, a fifth optical fiber may be optically aligned with a third optical element. In one embodiment, the first and second optical elements 128, 132 are beamsplitters. The first optical element 128 has a first port 129, a second port 131 and a common port 133. The first port 129 may, for example, be an input port, where excitation light from an excitation light source enters the first optical element 128, which may, for example, be a beam splitter. The excitation light exits the beam splitter via the common port 133. Light emitted from a test animal 104 enters the beam splitter 128 via the common port 133 and exits the beam splitter 128 via the second port 131. In the embodiment shown in FIG. 1A, the first optical fiber 122 extends between the rotatable arm 102 and the motorized arm 106. At a predetermined angular position of the motorized arm 102, the first optical fiber 122 is optically aligned with the first port 129 and the second port 131 via the common port 133 of the optical element 128.

The second optical element 132 also has a first port 135, a second port 137 and a common port 139. Similar to the first optical element 128, the third optical fiber 130 is optically aligned with a first port 135 and a second port 137 of the second optical element 132 via the common port 139. The first port 135 may, for example, be an input port, where excitation light from an excitation light source enters the second optical element 132, which may, for example, be a beam splitter. The excitation light exits the beam splitter 132 via the common port 139. Light emitted from a test animal 104 enters the beam splitter via the common port 139 and exits the beam splitter 132 via the second port 137.

While coupling to an optical beamsplitter is disclosed herein, it is expressly contemplated that a different optical element may be used instead of a beamsplitter. For example, a simple optical element could be used to collect light from the optics in the motorized disk 106 that is generated through a biological or chemical process in an animal without an excitation light source, enabling luminescence (bioluminescence, chemiluminescence) applications. Alternatively, the optical element may allow light to enter the optics in the motorized disk 106 as a collimated beam to turn on or off certain biological processes in the animal, enabling optogenetic activation or deactivation. The light source may be a laser or any other light source.

To maximize coupling efficiency through the free-space optical interface 126, the first end 134 of a first 122 (third, fifth, seventh, etc.) optical fiber is optically aligned with another optical element 150. This optical element 150 has a dual function: in the forward direction, it focuses the incoming excitation light to a spot that is aligned with the core of the optical fiber at the first end 134; in the reverse direction, it projects the emitted photons into a collimated beam toward the photon detector. To minimize misalignment, the fiber end 134 is coupled to the optical element 150 upon optical alignment. In different embodiments, the fiber end 134 may be removably coupled to the optical element 150 or permanently coupled to the optical element 150. An example of such an optical element 150 is a ball lens. Alternatively, any optical element 150 that performs the same dual functions can be used.

The second key aspect of the design disclosed herein is the use of two concentric arms or disks—one freely rotatable arm 102 (also referred to as the first arm) and one motorized arm 106 (also referred to as the second arm). It is to be noted that the structures that are herein described as arms may also be implemented as disks and vice versa. Also, while the terms "arm" and "disk" are used herein, it should be understood that these components may be any geometric shape or form that achieves the same function. For example, the first arm 102 and second arm 106 may be any shape that allows for movement around the motor shaft axis 124. In the embodiment shown in FIG. 1A, the rotatable arm 102 and the motorized arm 106 are both disk-shaped and the motorized arm 106 is axially spaced from the first arm 102 and coaxially disposed about the shaft 138, such that the shaft 138 can rotate independently of the motorized arm 106. In other embodiments in which the rotatable arm 102 and the motorized arm 106 are not disk-shaped, at least a portion of the rotatable arm 102 and motorized arm 106 extend radially from the shaft 138. In these embodiments, the motorized arm 106 is still axially spaced from the rotatable arm 102 and both arms 102, 106 rotate around the rotation axis 124 of the shaft 138.

The freely rotatable arm 102 is pulled by the animal's movements and causes the rotor 120 to rotate with it. The angular displacement of the rotor 120 with respect to a stator 136 is recorded by the angular encoder electronics module 141 which is communicably coupled to the stator 136. The motorized arm 106, with the motor shaft 138 going through its open center 140, is selectively immobilized and supported from below. When the angular encoder module 141 detects that the rotatable arm 102 reaches a certain threshold angle by rotating a predetermined amount, the processor 142 activates a clutch 144, which mechanically couples the motorized arm 106 to the motor shaft 138 to rotate. The processor 142 commands the motor 118 to rotate, which rotates the motorized arm 106, thereby unwinding the optical fibers 114, 116. The motor 118 may rotate the shaft 138 by the same predetermined amount as the threshold angle or by another predetermined amount. When the motor 118 stops, the clutch 144 is deactivated by the processor 142, and the motorized arm 106 detaches from the motor shaft 138 and returns to a well-defined stationary position.

In one embodiment, the clutch 144 is an electromagnet. When the processor 142 activates the electromagnet, the electromagnet lifts the motorized arm 106 from the support 146 thereby freeing the motorized arm 106 to rotate. When the processor 142 deactivates the electromagnet, the motorized arm 106 falls back to the support 146, which then again immobilizes the motorized arm 106.

In another embodiment, the clutch may have a clamp that is attached to the second arm 106 and can be configured to grab onto the motor shaft 138, thereby rotating the second arm 106.

Figures 3, 4:
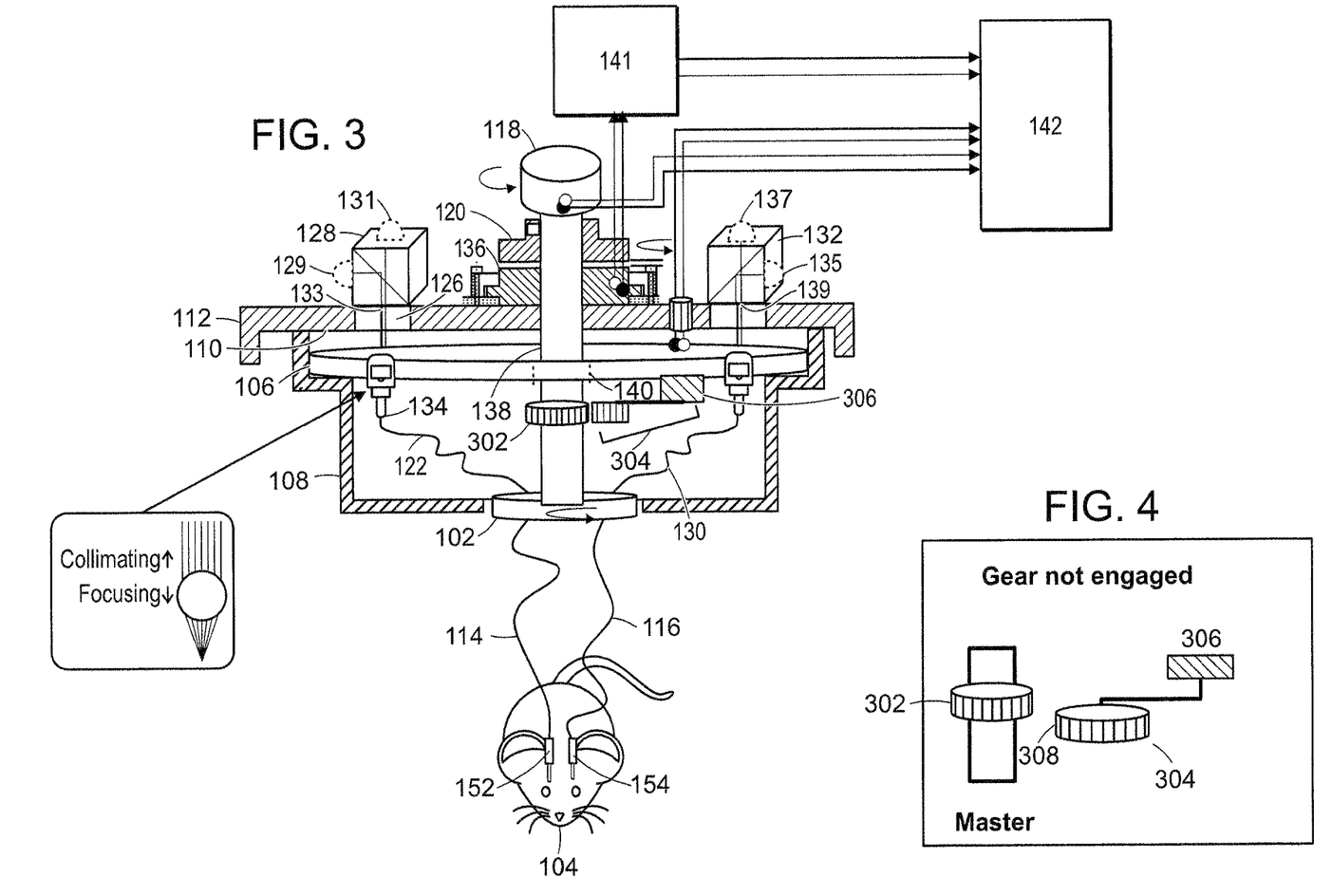
FIG. 3 depicts a side view of yet another embodiment of the present invention using a gear mechanism to engage the motorized arm.
FIG. 4 shows key components of the mechanism of FIG. 3 when the gear and servo horn are not engaged.

In another embodiment shown in FIGS. 3 and 4, the clutch may include a gear 302 attached to the motor shaft 138. A servo horn 304 is controlled by a servo motor 306 which is attached to the second arm 106. The servo horn 304 has at least one groove or at least one spoke that can engage with the gear 302. The servo horn 304 may be a toothed servo horn. In the default state shown in FIG. 4 in which the second arm 106 is stationary, the gear 302 is not engaged with the servo horn 304. Upon instruction from the processor 142, the servo motor 306 moves the servo horn 304 by an angle in the plane parallel to the plane of the second arm 106 such that the gear 302 and the servo horn 304 are engaged as shown in FIG. 3. In an embodiment in which the servo horn 304 includes at least one spoke or "tooth", the motor 306 moves the servo horn 304 to selectively engage the toothed end 308 to the gear 302.

Optionally, there may be an interlocking mechanism which is configured to maintain a calibrated position of the motorized arm 106 with respect to the first port 129 and the second port 131 of the optical element 128 when the clutch is disengaged. The interlocking mechanism allows for reproducible and accurate positioning and repositioning of the motorized arm 106. In one embodiment, there may be saw-tooth shaped structures on the bottom of the motorized arm 106 and on the top of the support for the motorized arm to provide such an interlocking mechanism. When the motorized arm 106 returns to a well-defined position, the sawtooth structures on the bottom of the motorized arm 106 align (individual teeth of the sawtooth structures interdigitate) with the sawtooth structures on the top of the support. In some embodiments, friction between the top of the support 146 and the bottom of the motorized arm 106 provides an interlocking mechanism. Alternatively, such an interlocking mechanism may include a V-shaped structure 143 on the arm or disk 106 combined with a complementary V-shaped notch 145 on the support 146. The interlocking mechanism may also be a conical piece on the arm or disk 106 combined with a conical hole on the support 146. The V-shaped structure or conical piece drops into the V-shaped notch or conical hole when the motorized arm 106 returns to its original stationary position. In some embodiments, friction between the top of the support 146 and the bottom of the motorized arm 106 provides an interlocking mechanism. The alignment mechanism ensures that the motorized arm 106 always returns to and maintains the well-defined optical alignment in x-y plane and its 45° angle with respect to the surface of the optical element 128 which may be a beam splitter. If the motorized arm 106 does not return to its original position, the light from the first port 129 of the optical element 128 will not substantially reach the fiber 122 and the return light from the optical fiber 122 will not substantially reach the second port 131 of the optical element 128. The optical alignment position is calibrated at set up.

Figure 1B:
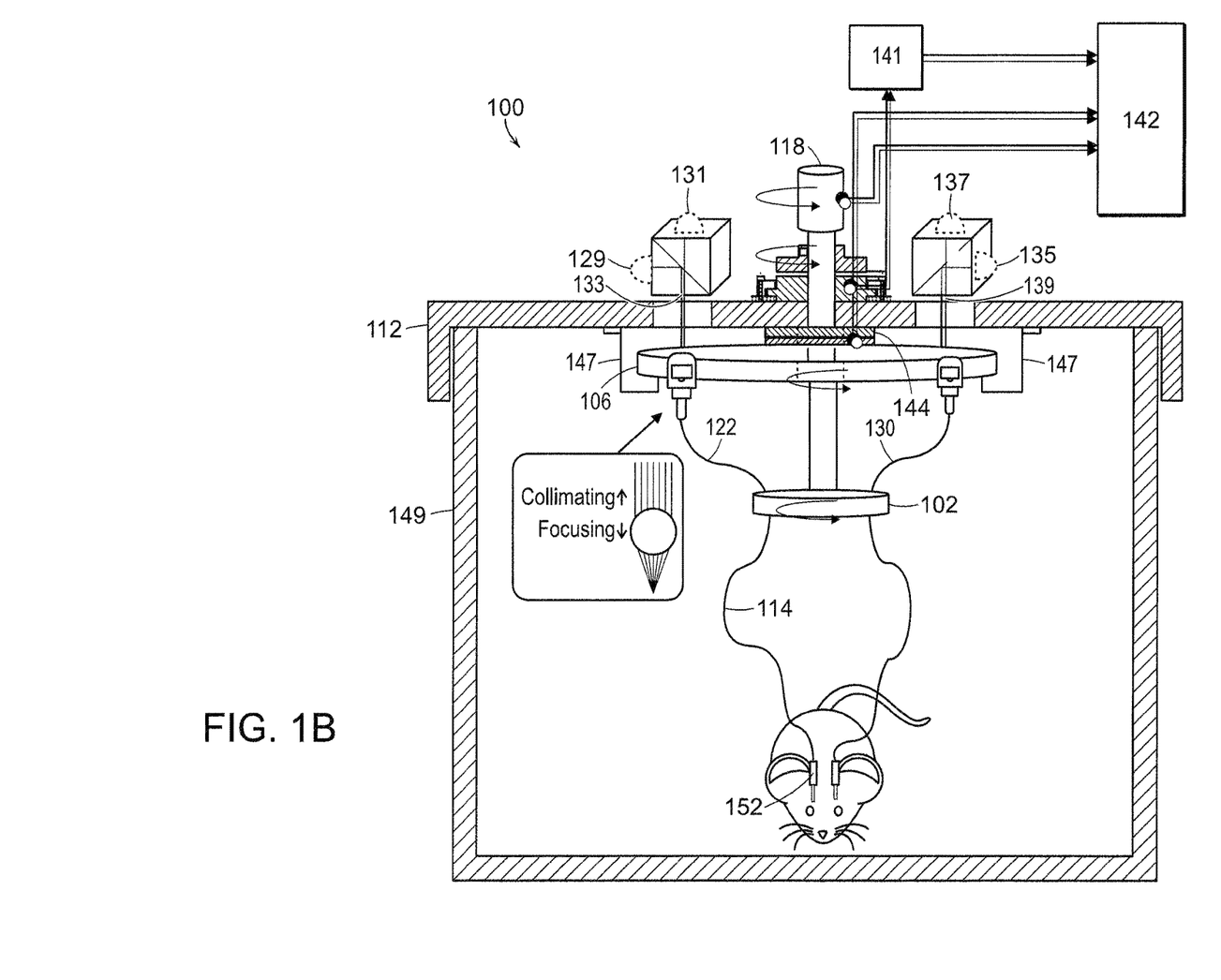
FIG. 1B depicts a side view of another embodiment of the present invention without a dark enclosure.

FIG. 1B depicts a side view of another embodiment of the present invention without the dark enclosure 108. In this embodiment, the supports 147 support the motorized arm 106 when not coupled to the motor shaft 138. FIG. 1B also shows the lid 112 on the cage 149.

The results of a simulation of the action of the FORJ in response to mouse movements during the development of the design disclosed herein are described in detail below. One conclusion is that it is not efficient to unwind every time the mouse makes a turn. In certain embodiments, it may be desirable for unwinding to take place every n number of net full turns. A 45° turn by the mouse to the left followed by a 45° turn to the right leads to a zero net turn. One net full (360°) turn is typically the result of many left and right mouse turns. The torsion in the optical fibers 114, 116 is released only when the net angular displacement reaches a user-defined threshold angle. Furthermore, it is important to note that one full turn on the fiber may translate to a fraction of 360° angular displacement between the rotor 120 and the stator 136, due to the stiffness of the optical fiber jacket. The relationship between angular displacement and the number of full turns on the fiber may be determined experimentally.

The third key aspect of the design disclosed herein is the use of a motor 118 with near zero resistance to rotation, i.e. a motor that has substantially no resistance to rotation. Exemplarily, the motor 118 may be a brushless DC motor. This implies that, for a small animal there is minimal resistance to rotate the thin and light weight rotatable arm or disk 102 when the motor 118 is not energized. This aspect of the design resolves the issue of a high starting torque, another key limitation in the current commercial FORJs.

Figure 2A:
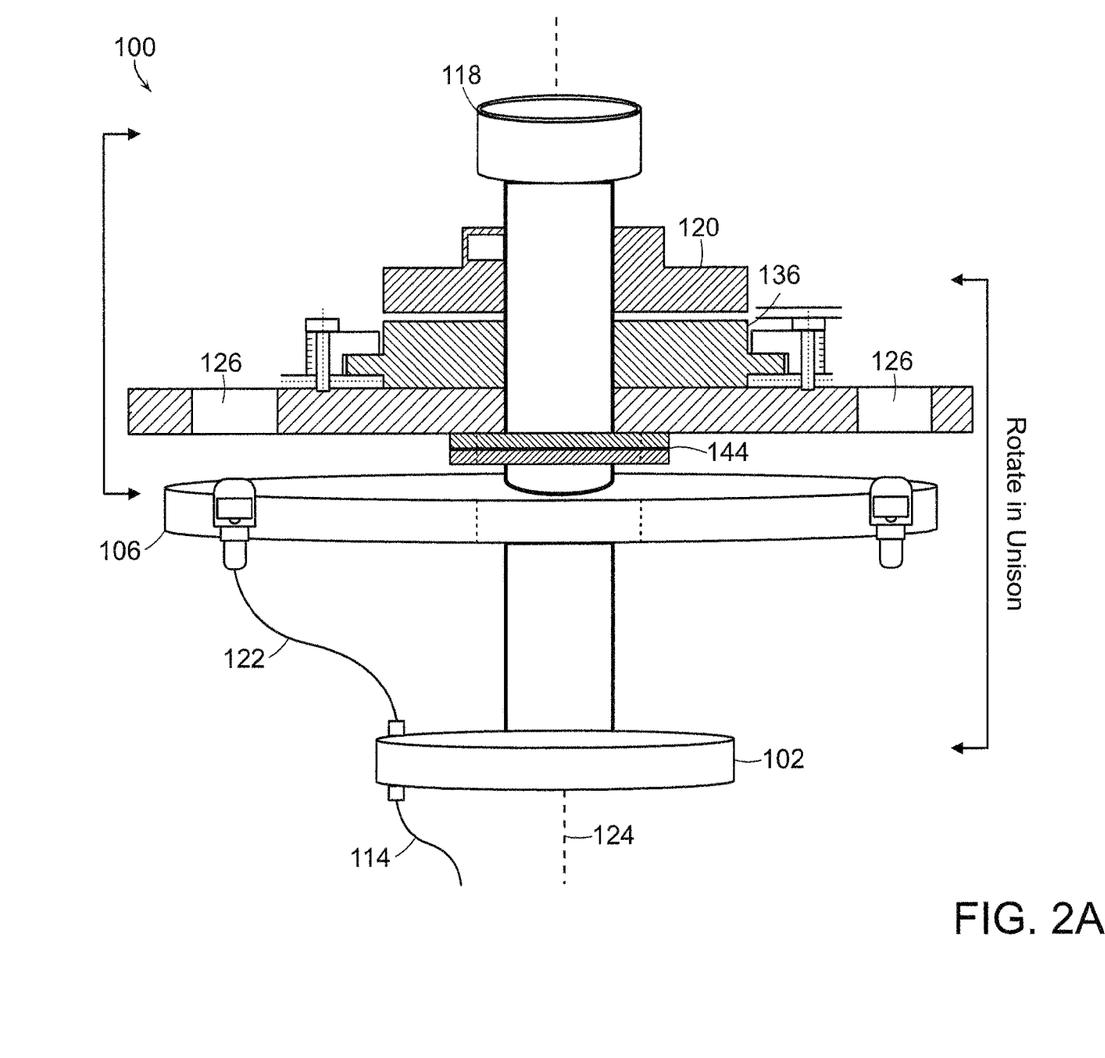
FIG. 2A shows key components and the working principle of an illustrative embodiment of the present invention.
Figure 2B:
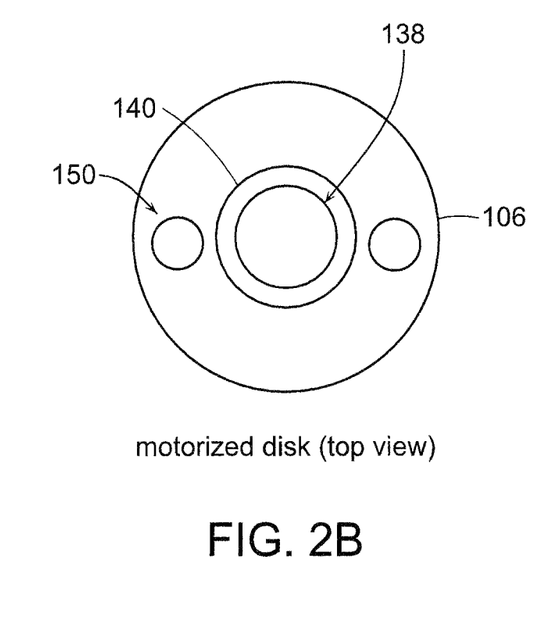
FIG. 2B depicts a top view of an embodiment of the motorized arm or disk of a two-channel FORJ.

FIGS. 2A and 2B show key components and the working principle of an illustrative embodiment of a FORJ 100 of the present invention. The movement of an animal causes the freely rotatable disk or arm 102 to rotate, which leads to the same angular displacement on the rotor 120. The rotatable disk or arm 102 is coupled with the rotor 120. The motorized disk or arm 106 can be coupled with the motor 118. The motorized disk or arm 106 unwinds at predetermined increments. In one embodiment, the motorized disk or arm 106 unwinds at increments of 360°.

Alternatively, the motorized arm or disk 106 may unwind at increments of a fraction n/m of 360°, where n is an integer and m is the number of channels. For example, in a two-channel FORJ setup, the motorized arm 106 may unwind at increments of ½ of 360°, i.e. 180°. This requires coordinating the FORJ processor 142 with the analysis software, because a given channel from the point of interest on the animal (such as a mouse brain) could be switched among the analysis channels. Unwinding at increments of 360° ensures that the relationship between channels from the mouse brain and analysis channels stays the same, e.g. a first channel from the mouse brain is connected to a first analysis channel, and a second channel from the mouse brain is connected to a second analysis channel. Unwinding at, for example, 180° would switch the first channel from the mouse brain to the second analysis channel and vice versa. This information can be communicated between the FORJ processor 142 and the analysis software so that the channels recorded or processed in the analysis stay the same.

The complete light path is as follows: A collimated light beam enters the optical element 128. In one embodiment, the optical element 128 is a long pass dichroic beam splitter unit. After reflecting off of the dichroic mirror 128, it passes through the free-space 126 between the beam splitter 128 and the motorized (second) arm 106. Then it enters the optics 150 that focuses the collimated beam onto the center of the fiber 122. Bidirectional optics are pre-assembled with the fiber and then seated into the motorized arm or disk 106. In the reverse direction, the emitted fluorescence photons are collected by the implanted fiber. The emitted light travels back through the fiber 122 towards the bidirectional optics 150 and is projected as a collimated beam toward the dichroic beam splitter 128. It is important to note that, although the free-space optical coupling is shown having an optical axis parallel to the rotational axis of the shaft and two arms/disks 102, 106, the optical axis of the free-space coupling can be non-parallel to the rotational axis.

The distal ends 152, 154 of each fiber output can be any type of a fiber-ferrule that is connected to a matching type fiber ferrule implanted in an animal (in the brain or another anatomical region of interest). The connection between the two components can be mechanical or magnetic by which the optical alignment is optimized for maximal light throughput and minimal optical artifacts. The flexibility of disconnecting the fiber assemblies from the fiber implants allows intermittent measurements (minutes or hour) over long term experiments (weeks). Alternatively, the optical fiber from the rotatable disk can be terminated with a fiber ferrule that can be directly implanted in a small animal like a mouse. How the optical fiber is connected to a small animal is determined by the need of a user.

Light of various wavelengths can be delivered, thus allowing different fluorophores to be detected. Software running on a computer can then be utilized to coordinate the FORT with data acquisition.

Figure 5A:
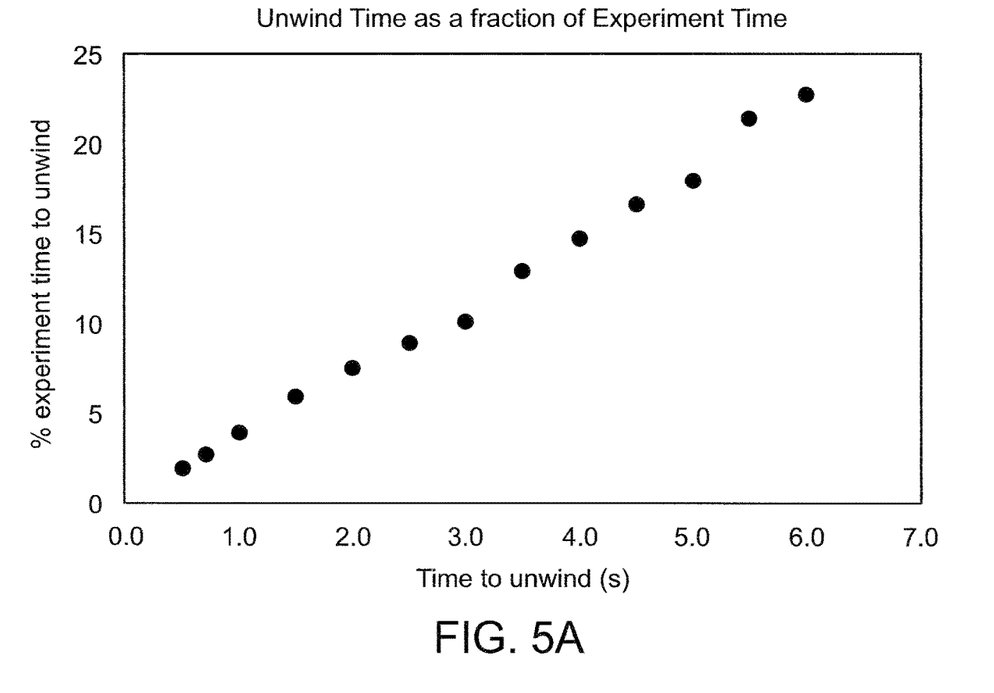
FIG. 5A shows the results of numerical simulation of the effect of the duration to unwind on the percent time spent on unwinding.
Figure 5B:
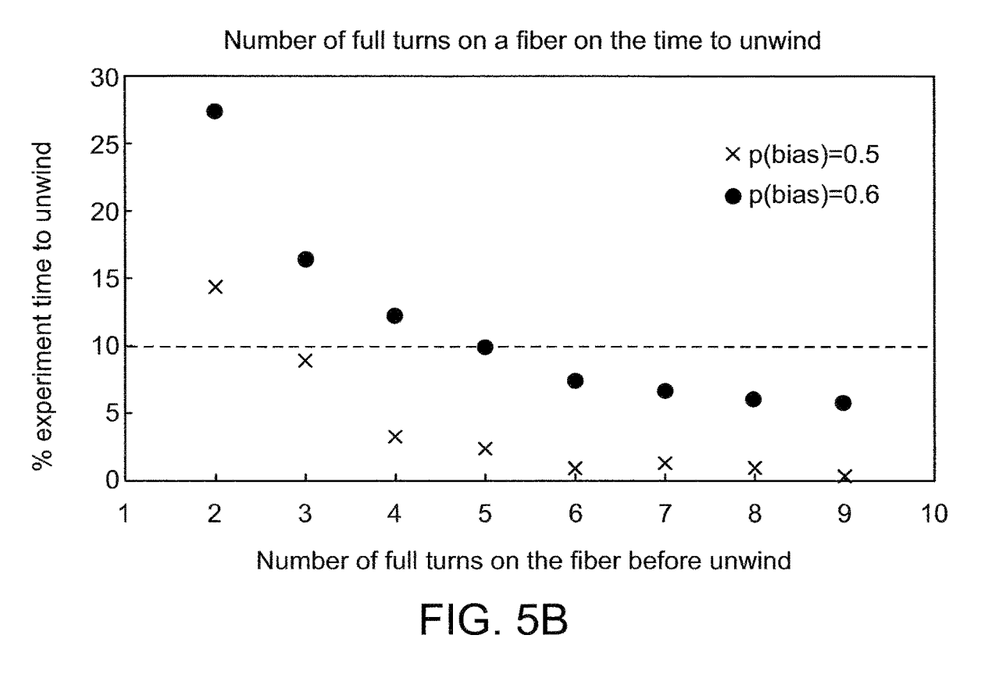
FIG. 5B shows the results of numerical simulation of the effect of the turning bias on the percent time spent on unwinding.

To optimize the design, the inventors carried out numerical simulations to assess the effects of duration and frequency of unwinding, and turning bias and restlessness of a mouse, on the fraction of total experimental time that the FORT is activated. The simulation took into consideration the turning bias (i.e. greater than 50% probability of making a turn in one direction over the other), the mouse movement frequency (per second), the number of full turns on the fiber before unwinding, and the duration of unwinding. FIGS. 5A and 5B show the results of numerical simulation of the effect of the duration to unwind (FIG. 5A) and of the turning bias (FIG. 5B) on the percent time spent on unwinding during an experiment. For a given mouse movement frequency, the results of the simulation show (1) that turning bias has a strong effect on the percent of time spent on unwinding in an experiment (FIG. 5B); (2) that the time it takes to unwind needs to be minimized; (3) that it is desirable to use soft and flexible fiber cable so as to reduce the frequency of unwinding. Finally, it is also clear from the simulation that the higher the frequency of the mouse movement, the higher percentage of time of unwinding is in the total time.

Four-Channel FORJ

To build a four-channel FORJ, in one embodiment two additional optical elements such as dichroic beam splitter units and two detectors are added to the design disclosed above. The motorized disk or arm 606 then has two additional fiber-coupled optics, as shown in FIG. 6.

Figure 6:
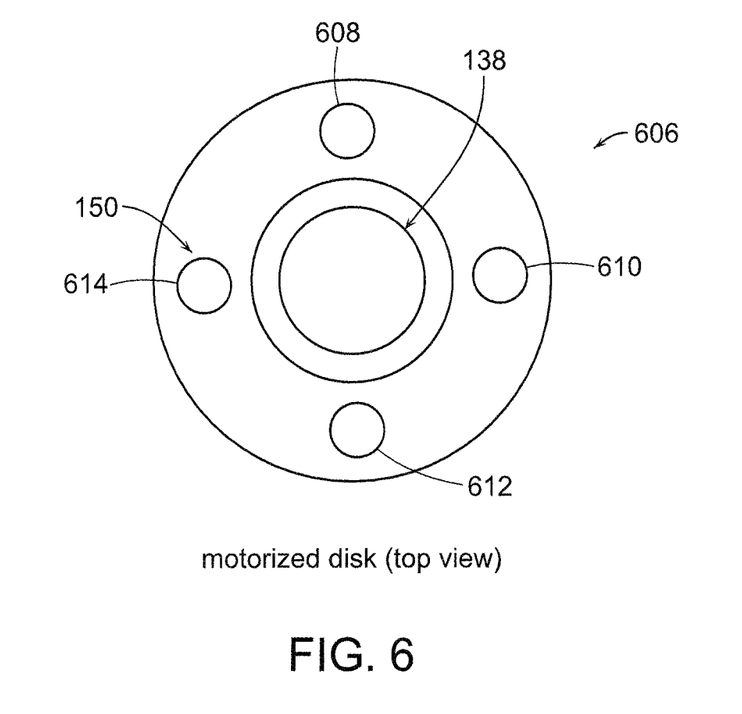
FIG. 6 depicts a top view of another embodiment of the motorized arm or disk of a four-channel FORJ.

FIG. 6 depicts a top view of the motorized arm or disk 606 containing four optical elements 608, 610, 612, 614, one for each detection channel. The rotatable arm or disk 606 allows four fibers to be affixed to it. The design disclosed herein allows easy scale-up to more channels.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

While the terms "mouse" and "rodent" have been used herein, it should be understood that the invention can be used with any animal.

As used herein, including in the claims, the term "brain" is used as an example only. The invention may be used to study any anatomical region of interest.

As used herein, including in the claims, the term "neuroscience" is not meant to limit the applicability of the claimed invention to only that field. The claimed invention could be used in any field of the life sciences.

Although aspects of embodiments may be described with reference to flowcharts and/or block diagrams, functions, operations, decisions, etc. of all or a portion of each block, or a combination of blocks, may be combined, separated into separate operations or performed in other orders. References to a "module" are for convenience and not intended to limit its implementation. All or a portion of each block, module or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The control of the FORJ disclosed herein, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective arms, disks, optical fibers, optical elements, etc. from one another and are not intended to indicate any particular order or total number of arms, disks, optical fibers, or optical elements in any particular embodiment. Thus, for example, a given embodiment may include only a second optical fiber and a third optical fiber.

What is claimed is:
1. An automated fiber optic rotary joint, comprising:
a processor;
an electric motor communicably coupled to the processor for control thereby;
a shaft mechanically coupled to the electric motor for rotation thereby;
a sensor configured to detect angular position of the shaft and communicably coupled to the processor to provide information about the angular position of the shaft to the processor;
a first arm rigidly attached to the shaft for rotation therewith;
a second arm axially spaced apart from the first arm and coaxially disposed about the shaft, such that the shaft can rotate independently of the second arm;
a clutch coupled to the processor for control thereby and configured to mechanically couple the second arm to the shaft for rotation therewith, when the clutch is engaged;
an interlocking mechanism configured to maintain a position of the second arm when the clutch is disengaged;
a first optical element having a first port, a second port and a common port; and
a first optical fiber extending between the first arm and the second arm, such that at a predetermined angular position of the second arm, a first end of the first optical fiber is optically aligned with a first port and a second port of the first optical element via a common port of the first optical element;

wherein the processor is configured to automatically use the information about the angular position of the shaft to determine whether the first arm has rotated by at least a first predetermined amount and, if the processor detects that the shaft has rotated by at least the first predetermined amount:
cause the clutch to engage;
cause the motor to rotate the shaft a second predetermined amount in a direction same as rotation of the first arm; and
cause the clutch to disengage.

2. An automated fiber optic rotary joint, comprising:
a processor;
an electric motor communicably coupled to the processor for control thereby;
a shaft having a longitudinal rotation axis and being mechanically coupled to the electric motor for rotation thereby about the rotation axis;
a sensor configured to detect angular position of the shaft, the sensor being communicably coupled to the processor to provide information about the angular position of the shaft to the processor;
a first arm extending radially from the shaft and attached to the shaft for rotation therewith about the rotation axis;
a second arm axially spaced along the rotation axis apart from the first arm, the second arm extending radially from the shaft and being configured to rotate about the rotation axis independently of the first arm;
a clutch coupled to the processor for control thereby and configured to mechanically couple the second arm to the shaft for rotation therewith when the clutch is engaged;
an interlocking mechanism configured to maintain a position of the second arm when the clutch is disengaged;
a first optical element having a first port, a second port and a common port; and
a first optical fiber extending between an eccentric, relative to the rotation axis, portion of the first arm and a portion of the second arm, such that at a predetermined angular position of the second arm, a first end of the first optical fiber is optically aligned with a first port and a second port of the first optical element via a common port of the first optical element;
wherein the processor is configured to automatically use the information about the angular position of the shaft to detect if the first arm has rotated by at least a first predetermined amount and, if so:
cause the clutch to engage;
cause the motor to rotate the shaft a second predetermined amount in a direction same as rotation of the first arm; and then
cause the clutch to disengage.

3. An automated fiber optic rotary joint according to claim 1, wherein the motor comprises a motor having substantially no resistance to rotation.

4. An automated fiber optic rotary joint according to claim 1, wherein the first optical fiber is replaceably attached to the first arm and to the second arm.

5. An automated fiber optic rotary joint according to claim 1, further comprising a second optical fiber, a first end of which is optically coupled to a second end of the first optical fiber, the second optical fiber extending from the first arm.

6. An automated fiber optic rotary joint according to claim 5, wherein the second optical fiber is replaceably attached to the first arm.

7. An automated fiber optic rotary joint according to claim 6, wherein a second end of the second optical fiber is configured to be implanted in a living animal at a region of interest.

8. An automated fiber optic rotary joint according to claim 7, wherein a second end of the second optical fiber is configured to be implanted in a living animal brain.

9. An automated fiber optic rotary joint according to claim 6, wherein a second end of the second optical fiber is configured to be coupled to an implant in a living animal at a region of interest.

10. An automated fiber optic rotary joint according to claim 9, wherein a second end of the second optical fiber is configured to be coupled to an implant in a living animal brain.

11. An automated fiber optic rotary joint according to claim 1, wherein the second predetermined amount is about an integer multiple of 360°.

12. An automated fiber optic rotary joint according to claim 1, wherein the second predetermined amount is about a fraction n/m of 360° and wherein n is an integer and m is a number of analysis channels.

13. An automated fiber optic rotary joint according to claim 1, further comprising:
a frame member configured to support the second arm; and
the clutch comprises an electromagnet configured to raise the second arm from the frame member.

14. An automated fiber optic rotary joint according to claim 13, wherein the second arm has a bottom and the frame member has a top and wherein structures are formed on the bottom of the second arm and on top of the frame member that allow for reproducible and accurate positioning and repositioning.

15. An automated fiber optic rotary joint according to claim 13, wherein any of the surfaces from the second arm form complimentary structures with the opposing surface of the frame member that allow for reproducible and accurate positioning and repositioning.

16. An automated fiber optic rotary joint according to claim 1, further comprising:
a second optical element having a first port, a second port and a common port; and
a third optical fiber extending between the first arm and the second arm, such that at the predetermined rotational position of the second arm, a first end of the third optical fiber is optically aligned with the first port and the second port via the common port of the second optical element.

17. An automated fiber optic rotary joint according to claim 16, further comprising:
a third optical element having a first port, a second port and a common port; and
a fifth optical fiber extending between the first arm and the second arm, such that at the predetermined rotational position of the second arm, a first end of the fifth optical fiber is optically aligned with the first port and the second port via the common port of the third optical element.

18. An automated fiber optic rotary joint according to claim 1, wherein the second arm is configured such that, at the predetermined rotational position of the second arm, the first end of the first optical fiber is optically coupled via free space with the first port and the second port via the common port of the first optical element.

19. An automated fiber optic rotary joint according to claim 1, wherein the first arm comprises a first disk and the second arm comprises a second disk.

20. An automated fiber optic rotary joint according to claim 1, wherein the first optical element comprises a beam splitter.

\* \* \* \* \*